United States Patent [19]

Buelna

[11] Patent Number: 5,242,459
[45] Date of Patent: Sep. 7, 1993

[54] DEVICE AND METHOD FOR APPLYING A LIGATING LOOP

[75] Inventor: Terry Buelna, Rancho Santa Margarita, Calif.

[73] Assignee: Laparomed Corporation, Irvine, Calif.

[21] Appl. No.: 911,834

[22] Filed: Jul. 10, 1992

[51] Int. Cl.⁵ ............................................. A61B 17/00
[52] U.S. Cl. ..................................... 606/148; 606/139; 606/170
[58] Field of Search .............. 606/139, 144, 148, 170, 606/181, 182, 187

[56] References Cited

U.S. PATENT DOCUMENTS

| | | |
|---|---|---|
| 2,268,755 | 1/1942 | Li . |
| 2,316,297 | 4/1943 | Southerland et al. ............... 606/139 |
| 2,433,956 | 1/1948 | Miller . |
| 2,455,833 | 12/1948 | Trombetta . |
| 2,610,631 | 9/1952 | Calicchio . |
| 3,476,115 | 11/1969 | Graeff et al. . |
| 4,018,229 | 4/1977 | Komiya . |
| 4,038,988 | 8/1977 | Perisse . |
| 4,050,465 | 9/1977 | Perisse . |
| 4,126,124 | 11/1978 | Miller ................................... 606/187 |
| 4,177,813 | 12/1979 | Miller et al. . |
| 5,037,433 | 8/1991 | Wilk et al. ............................ 606/144 |
| 5,129,912 | 7/1992 | Noda et al. .......................... 606/148 |
| 5,133,723 | 7/1992 | Li et al. ................................ 606/139 |
| 5,176,691 | 1/1973 | Pierce .................................. 606/144 |

Primary Examiner—Stephen C. Pellegrino
Assistant Examiner—Jeffrey A. Schmidt
Attorney, Agent, or Firm—Townsend and Townsend Khourie and Crew

[57] ABSTRACT

A suture applying device comprises an elongate shaft having a slidably mounted cutting member. A pre-tied suture loop is held at the distal end of the shaft with a free end of the suture being attached to a body member which is slidably received over the shaft. The cutting member is secured to the shaft by a link which collapses under a predetermined compressive force, causing the cutting member to move distally forward relative to the shaft to sever the free end of the suture. In this way, the suture loop can be initially tightened and subsequently severed by simply retracting the body member relative to the shaft in a single motion.

17 Claims, 3 Drawing Sheets

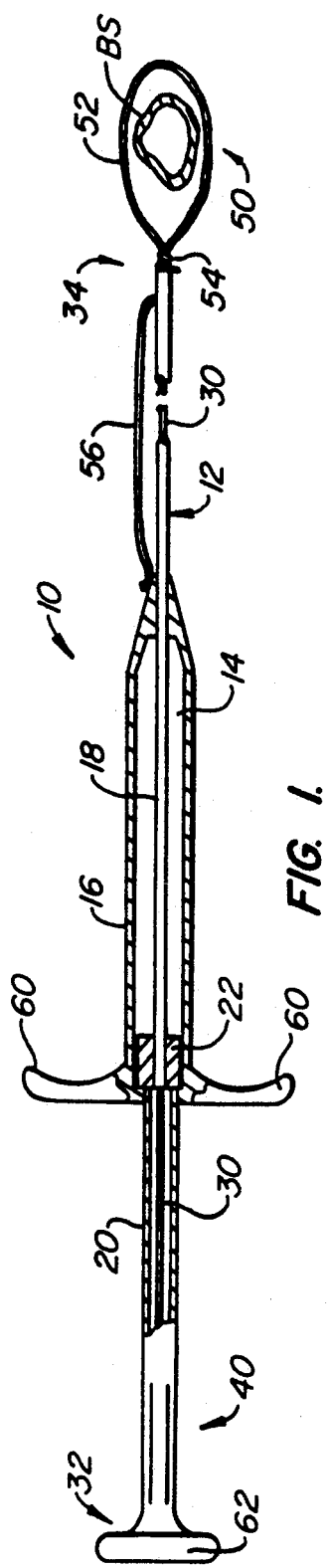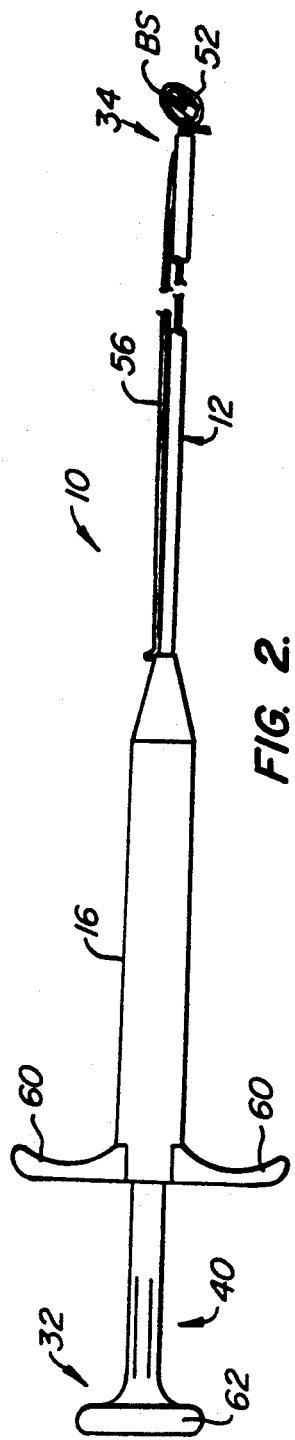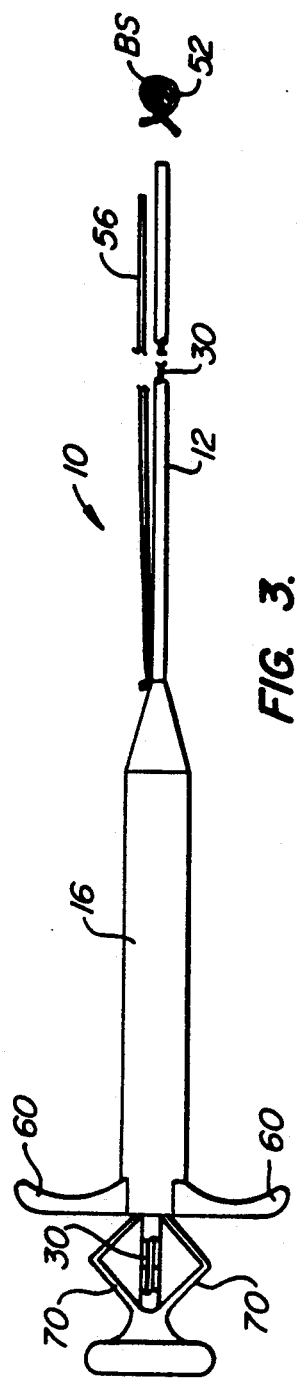

DEVICE AND METHOD FOR APPLYING A LIGATING LOOP

BACKGROUND OF THE INVENTION

Field of the Invention

The present invention relates generally to devices and methods for ligating body structures and, more particularly, to devices and methods for positioning a preformed ligating loop around the body structure, tightening the loop, and severing the loop from the device, where the user need only perform a single motion with the device.

Pre-tied ligating loops are utilized in surgical procedures for a variety of purposes. Most commonly, the ligating loops will be placed around the outside of a severed body lumen, such as a blood vessel or the cystic duct, tightened by pulling on a free end of the ligature, and severed, typically using separate severing shears. Often, the ligating loop will be mounted at the end of a rod or tube so that the surgeon may push on the knot with the tube while pulling on the free end of the ligature to tighten the loop.

While relatively easy to perform in open surgical procedures, the application, tightening, and cutting of pre-tied ligating loops is more problematic in laparoscopic and endoscopic procedures where the loop must be introduced and manipulated through a small incision, narrow trocar sleeve, or the like, while the surgeon views the procedure through an electronic imaging system. While the use of a pusher rod or tube facilitates such laparoscopic and endoscopic procedures somewhat, it is still necessary to sever the loop from the free end of the ligature after tightening. Generally, this has required the introduction of a separate cutting device, usually through a second incision or trocar sleeve.

For these reasons, it be desirable to provide improved devices and methods for applying pre-tied ligating loops to body structures, where the application, tightening, and severing steps described above can be performed using a single instrument. It would be particularly desirable if the single instrument could be manipulated using one hand and if the steps of tightening and severing the ligating loop could be performed with a single motion of the hand. Such methods and devices should be suitable for open surgical procedures as well as for laparoscopic and endoscopic procedures, and should automatically provide for an appropriate degree of tightening of the pre-tied knot as the ligating loop is being tightened prior to severing.

Description of the Background Art

U.S. Pat. No. 3,476,115, describes a tubular device for applying a loop of suture, where a free end of the suture is attached to a frangible proximal end of the tube. The loop is tightened by breaking off the frangible end of the tube and pulling the free end of the suture tight. Separate scissors are used to cut the loop after tightening. U.S. Pat. No. 2,610,631, describes a ligating device where a loop having a pre-tied knot is tightened by retracting a slidable member which draws back a free end of the loop. No severing means is described. U.S. Pat. 4,038,988, discloses a ligating device where a ligating loop is tightened and severed by twisting a mechanism on the device. U.S. Pat. No. 2,455,833, describes a ligating device where forceps and a loop ejecting mechanism are coupled together by a spring, whereby the forceps may be retracted and the loop ejected in a single actuation of the device. Other ligating devices are described in U.S. Pat. Nos. 4,177,813; 4,050,465; 4,018,229; 2,433,956; and 268,755.

SUMMARY OF THE INVENTION

According to the present invention, a suture applying device comprises a shaft which carries a pre-tied suture loop at its distal end. A knot in the pre-tied tied suture loop is held by the shaft so that pulling back on a free end of the suture will tighten or close the loop about a body structure. A cutting member is mounted on or in the shaft so that the loop can be severed from the free end of the suture after tightening. The cutting member will typically be a rod slidably mounted in a lumen of the shaft, but could also be a sleeve or other structure intended to slide over the exterior of the shaft. A unitary mechanism is provided which permits the user a single motion to both pull back on the free end of the suture to tighten the loop and, after tightening, extend the cutting member to sever the loop. In this way, the user can manipulate the device, including positioning, tightening, and severing of the loop, using a single hand.

In the specific illustrated embodiment, the suture applying device further comprises a body member having an axial passage therethrough. The shaft is slidably disposed in the axial passage of the body member, and the shaft includes a side aperture near its distal end. The cutting element is a rod slidably disposed in the lumen of the shaft, and the rod includes a cutting edge at its distal end. The suture is held at the distal end of the shaft so that its free end passes first through the lumen, then outward through the side aperture, and finally is attached to the distal end of the body member. In this way, retracting the body member relative to the shaft will apply tension to the free end of the suture and tighten the loop. The cutting rod is coupled to the shaft so that initially, as the body member is retracted, there is no relative movement between the shaft and the cutting rod. After the suture has been tighten, however, a link between the shaft and the cutting rod collapses, causing the cutting rod to advance distally relative to the shaft so that the cutting edge shears against the aperture to sever the suture passing therethrough.

In a method according to the present invention, the preformed loop of suture is first positioned over a target body structure by manipulating the device, typically through a small incision, needle, introducer cannula or a trocar sleeve. After properly positioning the loop, the body member is retracted relative to the shaft to pull on the free end of the suture to close the loop over the body structure. After tightening the loop, the user continues to apply a retracting force on the body member, whereby the link between the shaft and the cutting rod is collapsed, causing the cutting rod to advance and sever the free end of the suture from the loop. Typical target body structures include the cystic duct, arteries, blood vessels in bowel resection and appendectomy, the appendix, bowel perforations, and the like.

BRIEF DESCRIPTION OF THE DRAWINGS

FIG. 1 illustrates a ligating suture device constructed in accordance with the principles of the present invention, shown with portions in section.

FIG. 2 illustrates a ligating suture device of FIG. 1, shown with a loop of suture having been tighten about a body structure.

FIG. 3 illustrates a ligating suture device of FIG. 1, shown with the loop of suture having been tightened about a body structure and having been severed from the device.

DESCRIPTION OF THE SPECIFIC EMBODIMENTS

Figure 4:
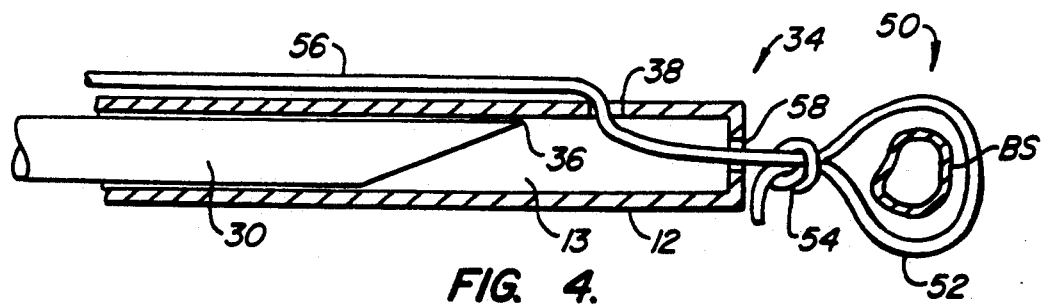
FIG. 4 is a detail view of the distal tip of the device shaft in the configuration of FIG. 1.

The suture applying device of the present invention comprises an elongate shaft which carries a suture loop at its distal end. The suture loop includes a pre-tied slip knot and a free end extending from the slip knot so that pulling on the free end in a proximal direction will tighten the loop over a body structure. The present invention further provides a cutting member which is automatically advanced relative to the shaft after the loop has been tightened by a predetermined amount, i.e. after the tension applied to the free end of the suture exceeds a predetermined threshold level. The free end of the suture will pass through a side aperture on the shaft so that axial advancement of the cutting member will sever the tightened loop from the free end. Thus, after manipulating the suture applying device to position the open loop over a desired body structure, the user need only apply tension to the free end of the loop to both tighten the loop over the body structure and subsequently advance the cutting member to sever the tightened loop from the device. By properly selecting the tension at which advancement of the cutting member is initiated, the loops can be automatically tightened to precisely the correct level.

The shaft of the suture applying device will be an elongate structure, typically being a tube or cylinder having a diameter small enough to be used in laparoscopic, endoscopic, and similar procedures. Typically, the shaft will have a width or diameter in the range from about 1.5 mm to 2.0 mm. The length of this shaft will also be sufficient to permit use of the device in laparoscopic, endoscopic, and similar procedures, typically being from about 20 cm to 30 cm, usually from 23 cm to 25 cm. It will be appreciated that the shaft diameter need not be uniform over its entire length and that the narrow diameter portion need only be long enough to permit access through a narrow incision or trocar sleeve being used in the procedure. The shaft may be composed of a variety of materials, usually being surgical stainless steel, polycarbonate resin, or the like.

The cutting member will also be an elongate structure, typically being a rod which is slidably received in an axial lumen of the shaft. Alternatively, the cutting member may be a cylindrical sleeve which is received over the exterior in the shaft, but this latter construction will generally be less preferred. In either case, the cutter member will have a cutting edge at its distal end so that axial movement of the cutting member will cause the cutting edge to pass the side aperture in the shaft, further causing a shearing action to sever the suture which passes through the aperture. The dimensions of the cutting member will be chosen to be compatible with the shaft, and the cutting member will usually be composed of surgical stainless steel, or the like.

The suture applying device of the present invention will usually further comprise a body member having an axial passage therethrough. The combination of shaft and cutting member will be slidably received through the axial passage, and the body member will receive the free end of the suture and will act as an anchor to apply tension to the free end of the suture as the shaft and cutting member are axially advanced (in a distal direction) relative to the body member.

Additional structure will be provided on both the shaft and the body member to permit the user to hold the suture applying device in one hand and to further apply a relative force to axially advance (i.e. in a distal direction) the shaft relative to the body member. Most simply, the structure may comprise a pair of finger retainers, i.e. "ears" or rings, disposed on a proximal end of the body member and a corresponding thumb retainer or ring disposed on the proximal end of the shaft. In this way, the user can hold the body member between the ring and the index finger while applying axial force on the shaft using the thumb. Alternatively, the structure could comprise a handle and lever which are operably attached to the body member and shaft so that squeezing of the lever relative to the handle will axially advance shaft. While these and other structures would be equally suitable, only the finger retainer and plunger structure is illustrated hereinafter.

In order to selectively advance the cutting member relative to the shaft, the cutting member is attached to the shaft through a collapsible link, such as a collapsible cage, a spring, a compliant rubber gasket, a wave washer, or the like. The collapsible link is sufficiently strong so that a cutting member will move in unison with the shaft while the suture loop is being tightened. Once tension on the free end of the suture exceeds a predetermined threshold level, however, the link structure will collapse so that the axial tension being applied to the shaft will axially advance the cutting member relative to the shaft. In this way, the cutting member will advance and sever the suture loop from the device only after sufficient tension has been applied to the suture to properly tighten the loop. The amount of force required to cause collapse of the link structure will depend on the type of slip knot chosen, the desired tightness of the slip knot, and the like, typically being in the range from about 0.25 lb. to 1 lb., usually being from 0.25 lb. to 0.5 lb.

Referring now to FIGS. 1–6, a specific embodiment 10 of the suture applying device of the present invention will be described. It will be appreciated, however, that the design details of the suture applying device may be modified significantly so long as the device, as a whole, performs the functions and objectives set forth above.

The suture applying device 10 comprises a shaft 12 received in an axial passage 14 of body member 16 (FIG. 1). The shaft 12 includes a narrow diameter cylindrical portion 18 and a larger diameter plunger portion 20. The plunger portion 20 is attached to the narrow diameter portion 18 through a sliding block member 22 which is received in the axial passage 14.

A cutting member 30 is coaxially received in a central lumen 13 (FIGS. 4–6) of the shaft 12 and extends from proximal end 32 location near distal end 34. As best seen in FIG. 4, the cutting member 30 terminates in a cutting edge 36 at a location on the distal side of a side aperture 38 in the shaft 12.

The shaft 12 further includes a collapsible link structure 40 near its proximal end. As illustrated, the link structure is an expandable cage defined by a plurality of axial slits within the wall of the shaft. It will be appreciated, however, that the collapsible structure could have a variety of other designs, such as a compression spring, a compliant rubber gasket, a wave washer, or the like.

Figure 5:
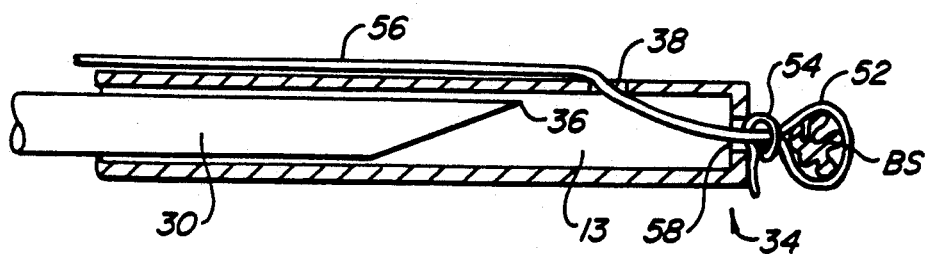
FIG. 5 is a detail view of the distal tip of the device shaft tip in the configuration of FIG. 2.
Figure 6:
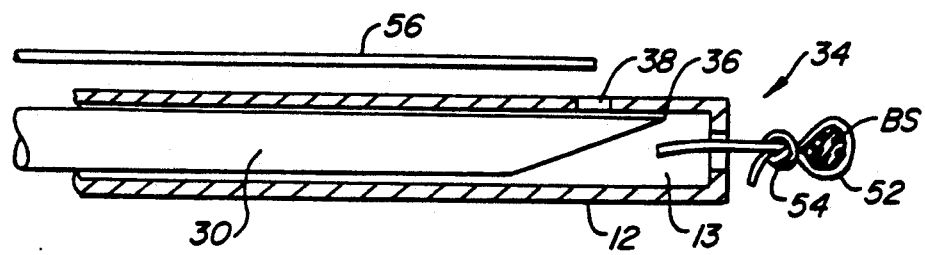
FIG. 6 is a detail view of the distal tip of the device shaft tip in the configuration of FIG. 3.

A length of suture 15 includes an open loop 52, a slip knot 54, and a free end 56. The open loop 52 is held outside the distal tip of shaft 12 with knot 54 being located adjacent an orifice 58 (FIGS. 4-6). The free end of suture 56 passes through the orifice 58 and into the lumen of the shaft 12. After passing through the lumen 13 in the proximal direction for a short distance, typically, about 1 cm, the free end 56 of the suture passes outward through the side aperture 38. The free end 56 then passes along the outside of the shaft 12 and is attached to a distal end of the body member 16 (FIGS. 1-3).

As illustrated in FIG. 1, the body member 6 of the suture applying device 10 is in a distally extended position. By "distally extended" it is meant that there is little or no tension being applied on the free end 56 of the suture 50. In this configuration, the loop 52 of suture 50 is sufficiently large to be positioned over a body structure BS, as illustrated in FIG. 1.

Tension may then be applied to the free end 56 of the suture 50 by moving the body member 16 in a proximal direction, i.e. to the left, as illustrated in FIG. 2. Conveniently, this is done by the user placing the index and ring fingers on lateral retaining members 60. By then depressing plunger 62 at the proximal end of shaft 12 using the thumb, the user can retract the body member 16 in a proximal direction.

Referring to FIG. 5, it can be seen that tension on the free end 56 of suture 50 tightens the loop 52 by drawing the free end back through the slip knot 54 which is held in place by orifice 58. After the loop 52 has been sufficiently tightened about body structure BS, tension applied by the free end 56 of the suture on the shaft 12 will increase above the minimum threshold level. The increase in tension on free end 56 of the suture, in turn, causes an increase in compression on the collapsible link 40, eventually causing axial elements 70 to expand, as illustrated in FIG. 3. Such expansion permits the plunger 62 to continue to travel in a distal direction relative to the remainder of shaft 12. The plunger 62 thus causes the cutting member 30 to axially advance in the distal direction, moving the cutting edge 36 forward past the side aperture 38, as illustrated in FIGS. 3 and 6. The cutting edge 36 moving past aperture 38 causes a shearing action which can sever the free end 56 of the suture from the tightened loop 52. In this way, the user is able to both tighten the suture loop 52 and sever the loop from the device 10 by simply advancing the plunger in a single action using a single hand. Moreover, by properly designing or "calibrating" the link 40 to collapse at a predesired level of compression, the tightening tension applied to free end 56 of the suture can be adjusted to provide a desired degree of tightening in the loop 52 and knot 54.

Figure 7:
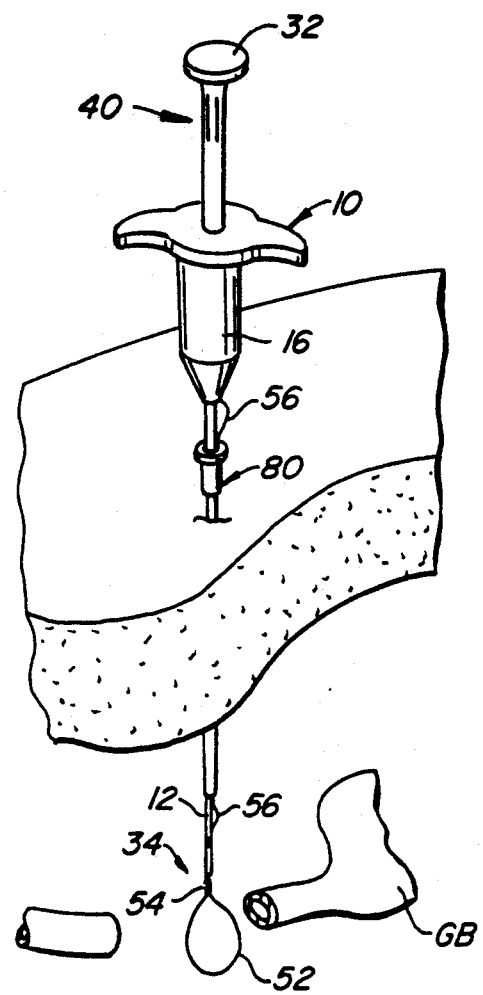
FIGS. 7 and 8 illustrate use of the suture applying device of the present invention in applying a loop of suture to a severed gallbladder in a laparoscopic cholecystectomy procedure.
Figure 8:
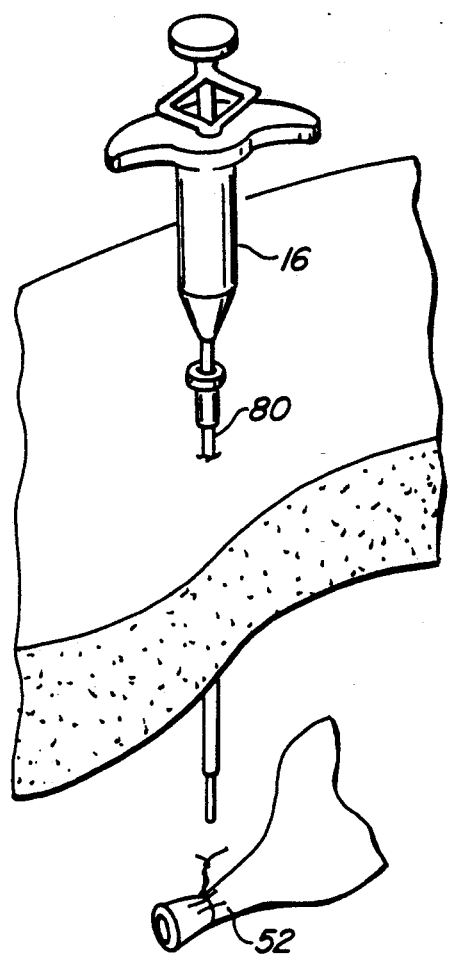

Referring now to FIGS. 7 and 8, use of the suture applying device 10 of the present invention for applying and tightening a suture loop 52 over a severed opening of a gallbladder is illustrated. The gallbladder GB will have been severed during a laparoscopic cholecystectomy procedure, as is now well described in the medical and patent literature. The suture applying device 10 is inserted through an introducer 80 (which is conveniently a 14 ga. introducer) which will have been percutaneously introduced by conventional techniques. The device 10 is inserted through the trocar sleeve 80 with the plunger 32 being distally retracted so that little or no tension is applied to the free end 56 of the suture. Device 10 is then manipulated so that the loop 52 is positioned over the gallbladder GB opening. After proper positioning, the user retracts the body member 16 proximally relative to the plunger 32 so that the distal tip 34 of shaft 12 remains generally in place while the body member 16 moves upward.

During the first portion of the upward travel of body member 16, the loop 52 is tightened by pulling free end 56 of the suture through the slip knot 54. After the loop 52 becomes tightened, however, the free end 56 of suture will inhibit further upward travel of the body member, and the collapsible cage structure 40 will be subjected to considerable compressive forces. By continuing to pull up on the body member 16, the axial segments 70 of the cage structure 40 will be caused to flare outward, as illustrated in FIG. 8, resulting in distal axial translation of the cutting member 30 and severing of the free end 56 of the suture, as illustrated in FIG. 6. As a result, the tightened loop 52 is released from the distal end 34 of the suture applying device 10. The device 10 can then be withdrawn through the trocar sleeve 80.

Figure 9:
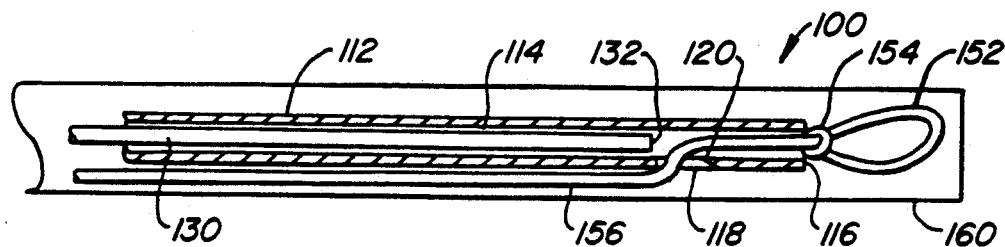
FIG. 9 illustrates an alternate embodiment of the suture applying device of the present invention.

FIG. 9 illustrates an alternate embodiment 100 of the suture applying device of the present invention. Only the distal portion of the device 100 is illustrated, with the proximal portions being generally the same as those illustrated in FIGS. 1-3. The device 100 includes a shaft 112 having an axial passage 114 terminating at a distal end 116. The shaft 112 includes a port 118 on its side, where the port 118 has a sharpened distal end 120. A cutting member 130 is provided in the form of a rod having a blunt tip 132, and suture 156 terminating in loop 152 is held in the shaft with knot 154 being disposed at the distal tip of the shaft and the free end of the suture passing through aperture 118. In this way, the blunt end 132 of cutting member 130 can engage the suture 156 and sever the suture in combination with the sharpened edge 120 of aperture 118.

The embodiment of FIG. 9 is particularly suitable in the construction of a partially reusable suture applying device. The suture 156 and shaft 114 could conveniently be provided as disposable components together with a reusable cutting member 130 which is attached to a body member and plunger assembly similar to that illustrated in FIGS. 1-3. Of course, the collapsible cage structure of FIGS. 1-3 would have to be replaced with a reusable structure, such as a spring having a spring force selected to permit actuation of the cutting member 130 after proper tensioning on the loop has been attained. The free end of the suture 156 could be attached to the remainder of the loop applying assembly, using a clip, collar, or similar attachable device.

In a preferred aspect, the suture applying device 100 could be introduced through a narrow gauge needle, such as a 13 gauge needle (not illustrated), typically using an outer protective sheath 160. The sheath 160 would be retractable to expose at least the loop structure 152 prior to use. A preferred knot 154 will be a Roeder knot, which is conventionally known in the art.

It will be appreciated that a variety of other specific cutting structures could be provided in the suture applying device of the present invention. The critical aspect of the present invention is that a relative axial motion between a cutting member and a shaft which carries the ligating loop be effected only after the loop has been properly tensioned. Most conveniently, this can be accomplished by passing the cutting member over an aperture in the shaft, where either the cutting member or the aperture is sharpened to effect the desired severing. A variety of other equally effective severing devices could be implemented, however, such as pivoted blades, concentric cylinders, adjacent blades, and the like.

Although the foregoing invention has been described in detail for purposes of clarity of understanding, it will be obvious that certain modifications may be practiced within the scope of the appended claims.

What is claimed is:

1. A suture applying device comprising:
    a shaft having a proximal end, a distal end, and a lumen therethrough;
    an elongate cutting member having a proximal end and a distal end, said cutting member being slidably mounted relative to the shaft;
    suture having a free end and a loop at another end, wherein the loop is held in the distal end of the shaft;
    means for applying tension to the free end of the suture to tighten the loop; and
    means, associated with the tension applying means, responsive to tension on the free end of the suture for advancing the curing member relative to the shaft to sever the suture after the loop has been tightened.

2. A suture applying device as in claim 1, wherein the means for applying tension to the suture is a body member having an axial passage which receives the shaft, wherein the free end of the suture is attached to the body member.

3. A suture applying device as in claim 1, wherein the elongate cutting member is slidably mounted within the lumen of the shaft and the means for advancing the cutting member relative to the shaft comprises a collapsible link between said cutting member and said shaft.

4. A suture applying device as in claim 3, wherein the collapsible link comprises an expandable cage structure formed integrally within the proximal end of the shaft.

5. A suture applying device as in claim 1, wherein the shaft has an outside diameter less than 5 mm.

6. A suture applying device comprising:
    a body member having an axial passage therethrough;
    a shaft slidably disposed in the axial passage of the body member, said shaft having a proximal end, a distal end, an axial lumen therethrough, and a side aperture near its distal end;
    a cutting rod slidably disposed in the lumen of the shaft, said rod having a proximal end and a distal end;
    suture having a free end and a loop at another end, wherein the loop is held in the distal end of the shaft and the free end passes through the aperture and is attached to the body member, whereby distally advancing the shaft will tighten the suture loop;
    means for distally advancing the shaft relative to the body; and
    means, coupling the cord to the shaft advancing means, for advancing the shaft and rod together until movement of the shaft is inhibited by tightening of the suture and for advancing only the cord thereafter, whereby the rod will advance relative to the shaft to sever the suture where it passes through the aperture.

7. A suture applying device as in claim 6, wherein the means for coupling the shaft advancing means and the rod comprises a collapsible link which connects the proximal end of the shaft to the proximal end of the rod.

8. A suture applying device as in claim 7, wherein the collapsible link comprises an expandable cage structure formed integrally within the proximal end of the shaft.

9. A suture applying device as in claim 6, wherein the means for distally advancing comprises a finger retainer on the body member and a thumb retainer on the proximal end of the shaft.

10. A suture applying device as in claim 6, wherein the distal end of the cutting rod is sharpened.

11. A suture applying device as in claim 6, wherein the side aperture is sharpened.

12. A suture applying device as in claim 6, wherein the shaft has an outside diameter less than 5 mm.

13. A method for applying suture to an animal body structure, said method comprising:
    positioning a preformed loop of suture over the animal body structure, said loop having a slip knot held at the distal end of a shaft and a free end attached to a device body member;
    retracting the device body member relative to the shaft to pull on the free end of the loop and tighten the loop over the animal body structure until moment of device body member relative to the shaft is inhibited by tensioning of the suture; and
    continuing to apply a retracting force to the body device member, whereby a portion of the shaft is collapsed to cause a rod mechanically coupled to the shaft to advance and sever the suture on a proximal side of the slip knot.

14. A method as in claim 13, wherein the positioning step comprises positioning the preformed loop of suture over a severed duct on the gallbladder.

15. A method as in claim 13, wherein the slip knot is held by tension in an aperture at the distal end of the shaft.

16. A method as in claim 13, wherein the free end of the suture is attached to a distal end of the body member and the body member is retracted by simultaneously pulling on the body member with fingers and pushing on the proximal end of the shaft with a thumb.

17. A method as in claim 16, wherein the portion of the shaft collapses with a tightening force of from 0.25 lb. to 1 lb.

* * * * *